(12) United States Patent
Robinson

(10) Patent No.: US 9,861,239 B1
(45) Date of Patent: Jan. 9, 2018

(54) TOILET SEAT WITH SANITIZING ULTRAVIOLET LAMP

(71) Applicant: Harry Robinson, Loxahatchee, FL (US)

(72) Inventor: Harry Robinson, Loxahatchee, FL (US)

( * ) Notice: Subject to any disclaimer, the term of this patent is extended or adjusted under 35 U.S.C. 154(b) by 115 days.

(21) Appl. No.: 15/064,232

(22) Filed: Mar. 8, 2016

(51) Int. Cl.
*A47K 13/02* (2006.01)
*A47K 13/30* (2006.01)
*A61L 2/10* (2006.01)

(52) U.S. Cl.
CPC ............ *A47K 13/302* (2013.01); *A47K 13/02* (2013.01); *A61L 2/10* (2013.01)

(58) Field of Classification Search
CPC .................................................. A47K 13/302
USPC ...................................................... 4/223–233
See application file for complete search history.

(56) References Cited

U.S. PATENT DOCUMENTS

| | | | | |
|---|---|---|---|---|
| 5,813,057 A * | 9/1998 | Descent | ............... | A47K 13/302 4/233 |
| 5,915,845 A * | 6/1999 | Lee | ............... | A47K 13/30 4/233 |
| 6,076,197 A * | 6/2000 | Yeung | ............... | A47K 13/302 4/233 |
| D596,723 S * | 7/2009 | Dempsey et al. | . | A41D 13/1209 D23/311 |
| 8,993,988 B2 * | 3/2015 | Nathan | ............... | A61L 2/0047 250/504 R |
| 2006/0021121 A1 * | 2/2006 | Moussa | ............... | A47K 13/302 4/233 |
| 2006/0097189 A1 * | 5/2006 | Lim | ............... | A47K 13/302 250/492.1 |
| 2007/0256226 A1 * | 11/2007 | Pinizzotto | ............... | A47K 13/302 4/420.4 |
| 2008/0000006 A1 * | 1/2008 | Ochoa | ............... | A41D 13/1236 2/114 |
| 2008/0000012 A1 * | 1/2008 | Adejare | ............... | A42B 1/041 2/171 |
| 2008/0134420 A1 * | 6/2008 | Ho | ............... | A47K 13/302 4/233 |
| 2008/0301867 A1 * | 12/2008 | Kemp | ............... | A47K 13/302 4/233 |
| 2009/0000007 A1 * | 1/2009 | DeMeo | ............... | A41D 13/1209 2/83 |
| 2010/0172290 A1 * | 7/2010 | Nam | ............... | H04L 1/1854 370/328 |
| 2010/0232382 A1 * | 9/2010 | Gauvreau | ............... | H04W 72/02 370/329 |
| 2011/0090825 A1 * | 4/2011 | Papasakellariou | ........ | H04L 1/06 370/280 |

(Continued)

FOREIGN PATENT DOCUMENTS

WO      9914443 A1      3/1999

*Primary Examiner* — Lori Baker
(74) *Attorney, Agent, or Firm* — Kyle A. Fletcher, Esq.

(57) ABSTRACT

The toilet seat with sanitizing ultraviolet lamp is adapted for use with a toilet. Specifically, the toilet seat with sanitizing ultraviolet lamp is designed to replace the existing seat on a toilet. The toilet seat with sanitizing ultraviolet lamp is made of a transparent material. Integrated into the structure of the toilet seat are a plurality of UV sources which generate ultraviolet light. The ultraviolet light is used to sanitize the toilet seat between uses. The toilet seat with sanitizing ultraviolet lamp comprises a toilet seat and a plurality of UV sources.

11 Claims, 6 Drawing Sheets

(56) References Cited

U.S. PATENT DOCUMENTS

| | | | |
|---|---|---|---|
| 2011/0134968 A1* | 6/2011 | Han | H04L 5/0023 375/146 |
| 2011/0268001 A1* | 11/2011 | Lee | H04L 5/0005 370/311 |
| 2012/0113948 A1* | 5/2012 | Kwon | H04L 1/0029 370/329 |
| 2012/0127869 A1* | 5/2012 | Yin | H04L 1/0031 370/252 |
| 2013/0148610 A1* | 6/2013 | Berggren | H04L 1/1692 370/329 |
| 2015/0055606 A1* | 2/2015 | Yang | H04L 1/1812 370/329 |

* cited by examiner

TOILET SEAT WITH SANITIZING ULTRAVIOLET LAMP

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of cleaning devices for sanitary equipment, more specifically, a disinfecting system for toilet seats.

SUMMARY OF INVENTION

The toilet seat with sanitizing ultraviolet lamp is adapted for use with a toilet. Specifically, the toilet seat with sanitizing ultraviolet lamp is designed to replace the existing seat on a toilet. The toilet seat with sanitizing ultraviolet lamp is made of a transparent material. Integrated into the structure of the toilet seat are a plurality of UV sources which generate ultraviolet light. The ultraviolet light is used to sanitize the toilet seat between uses.

These together with additional objects, features and advantages of the toilet seat with sanitizing ultraviolet lamp will be readily apparent to those of ordinary skill in the art upon reading the following detailed description of the presently preferred, but nonetheless illustrative, embodiments when taken in conjunction with the accompanying drawings.

In this respect, before explaining the current embodiments of the toilet seat with sanitizing ultraviolet lamp in detail, it is to be understood that the toilet seat with sanitizing ultraviolet lamp is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the toilet seat with sanitizing ultraviolet lamp.

It is therefore important that the claims be regarded as including such equivalent construction insofar as they do not depart from the spirit and scope of the toilet seat with sanitizing ultraviolet lamp. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

Figure 1:
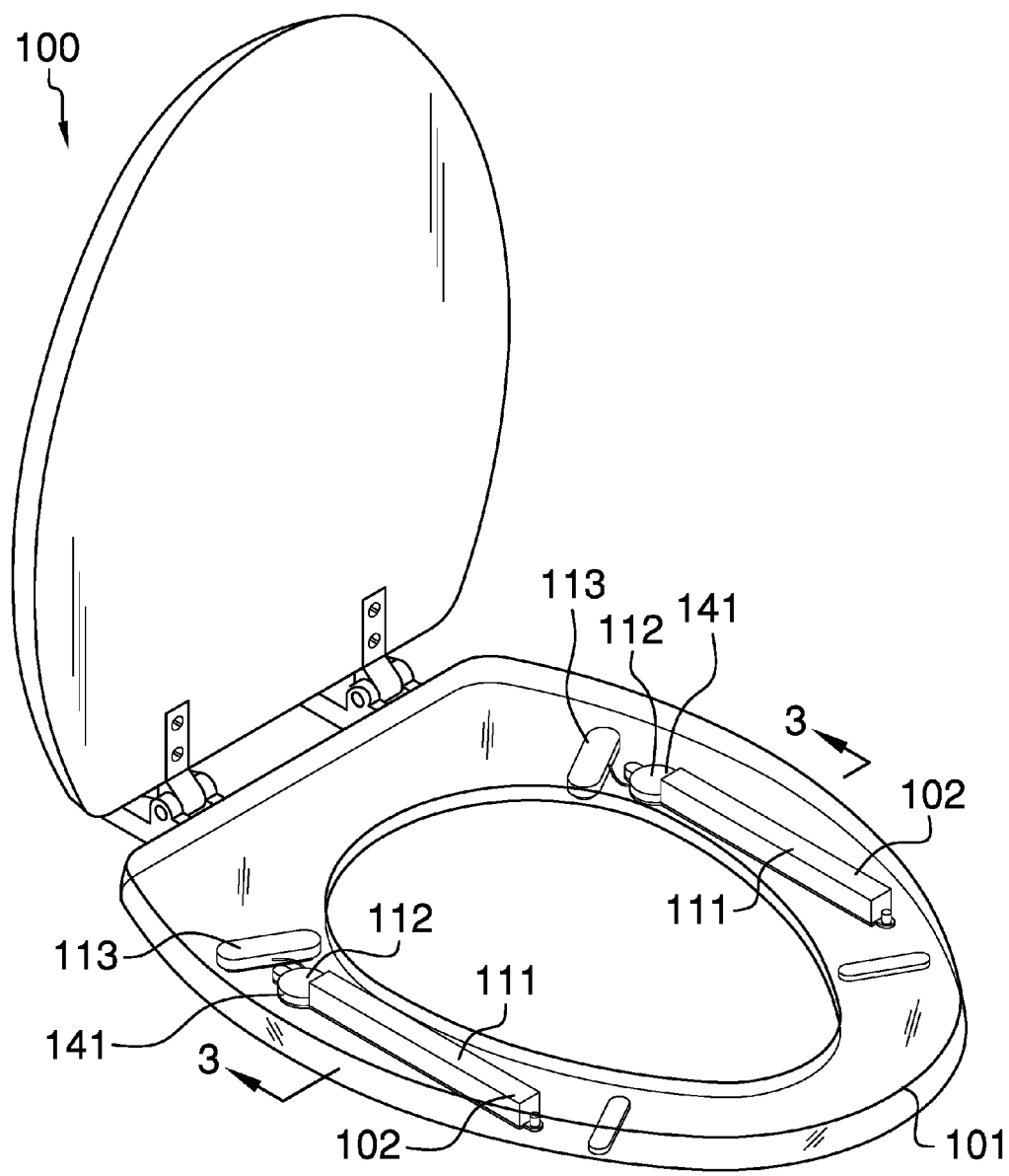
FIG. 1 is a perspective view of an embodiment of the disclosure.

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is no necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Detailed reference will now be made to a first potential embodiment of the disclosure, which is illustrated in FIGS. 1 through 6.

The toilet seat with sanitizing ultraviolet lamp 100 (hereinafter invention) comprises a toilet seat 101 and a plurality of UV sources 102. The invention 100 is adapted for use with a toilet 131. Specifically, the invention 100 is designed to replace the existing seat on a toilet 131. The invention 100 is made of a transparent material. Integrated into the structure of the toilet seat 101 are a plurality of UV sources 102 which generate ultraviolet light. The ultraviolet light is used to sanitize the toilet seat 101 between uses.

The toilet seat 101 is designed as a replacement for the traditional toilet seat used with toilets 131. The toilet seat 101 is molded from a transparent plastic. Suitable plastics include, but are not limited to, polycarbonate or poly(methyl methacrylic) The toilet seat 101 further comprises a plurality of UV chambers 121. Each of the plurality of UV chambers 121 is a cavity formed within the toilet seat 101 that is sized and designed to receive a UV source selected from the plurality of UV sources 102. Each UV source selected from the plurality of UV sources 102 is provided with a UV chamber selected from the plurality of UV chambers 121. Each UV chamber selected from the plurality of UV chambers 121 further comprises an individual UV cavity 122, an access port 123, and an access panel 124.

The individual UV cavity 122 is a hollow space that is formed within the toilet seat 101 that is sized to receive a UV source selected from the plurality of UV sources 102. The access port 123 is an aperture formed within the individual UV cavity 122 that provides access into the individual UV cavity 122. The access panel 124 is a barrier that is designed to fit over the access port 123 such that access into the individual UV cavity 122 through the access port 123 can be inhibited when the access panel 124 is in position. The access panel 124 is attached to the access port 123 using a latch or screw. Methods to form cavities, access ports, and latched panels in molded plastic structures are well known and documented in the art.

Each of the plurality of UV sources 102 generates an ultraviolet light for the purpose of sanitizing the toilet seat 101. Each of the plurality of UV sources 102 further comprises a UV lamp 111, a power source 112, and one or more sensors 113. The UV lamp 111 is a commercially available electrically powered UV lamp fixture that generates UV light. It is preferred that the selected UV lamp 111 generate ultraviolet C light. The power source 112 is a commercially available electrical power source that is used to power the UV lamp 111.

Figure 2:
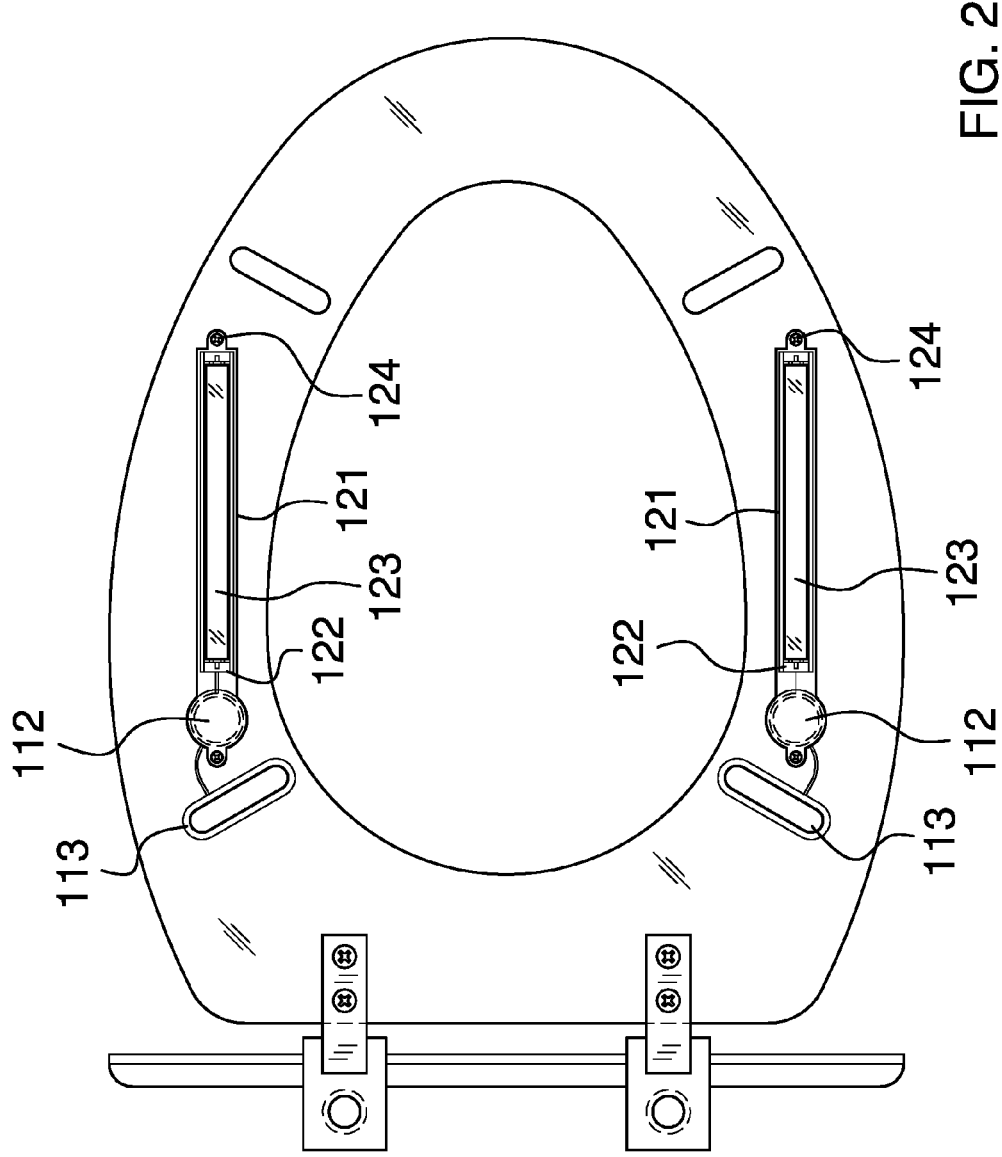
FIG. 2 is a bottom view of an embodiment of the disclosure.
Figure 3:
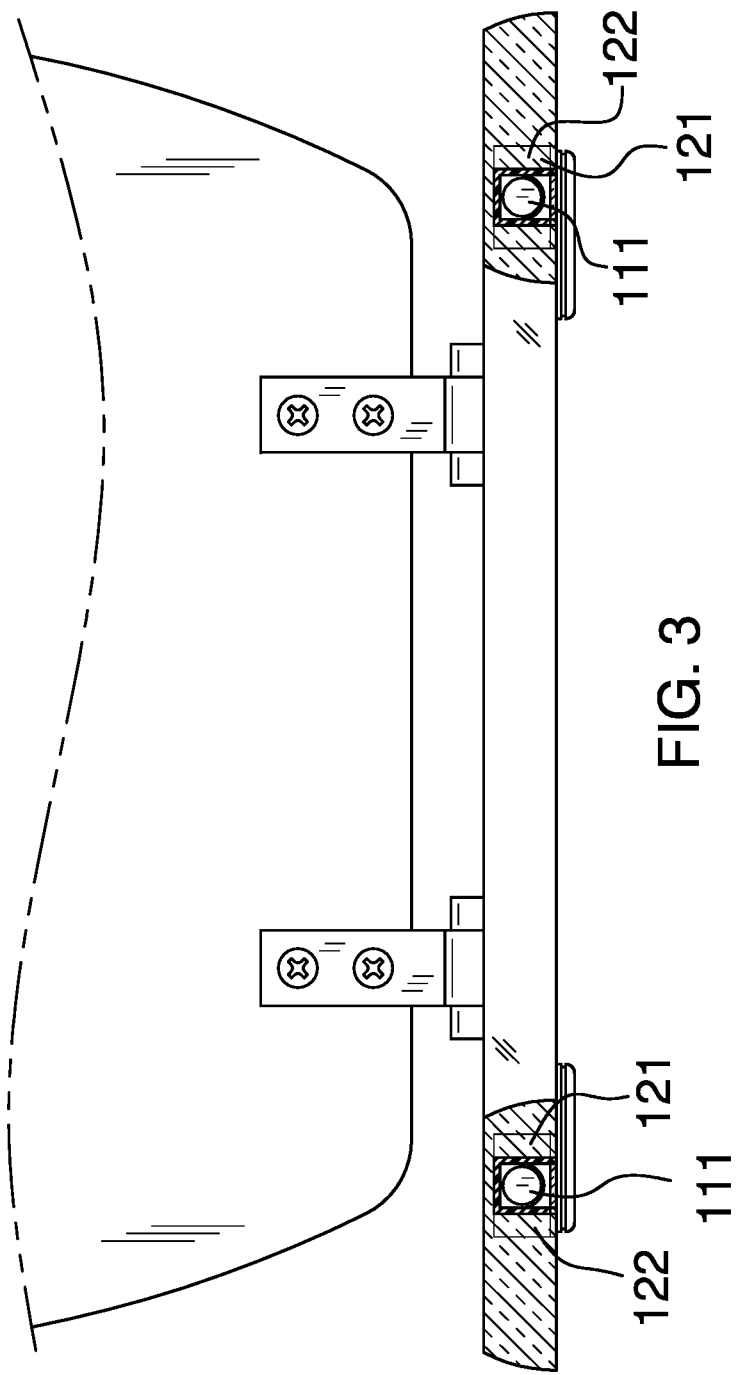
FIG. 3 is a front view of an embodiment of the disclosure.
Figure 4:
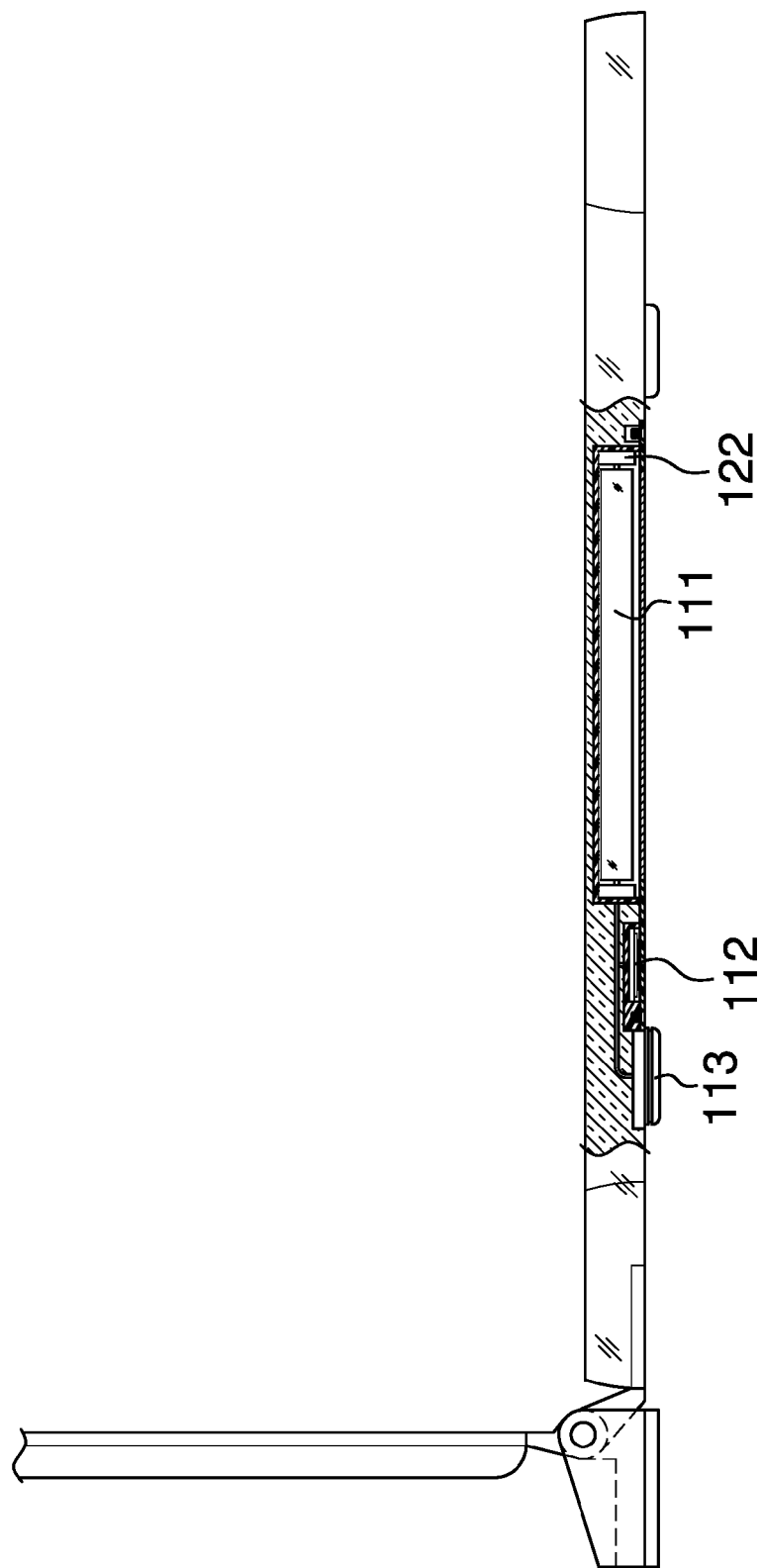
FIG. 4 is a side view of an embodiment of the disclosure.
Figure 5:
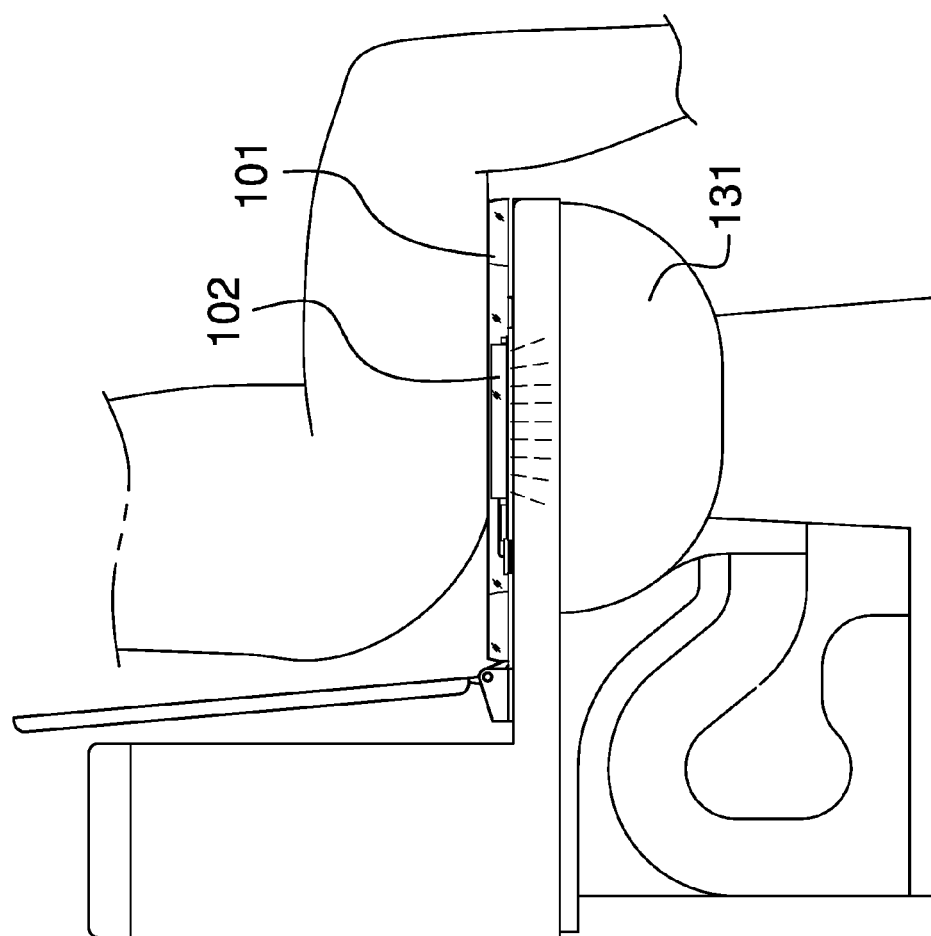
FIG. 5 is an in use view of an embodiment of the disclosure.
Figure 6:
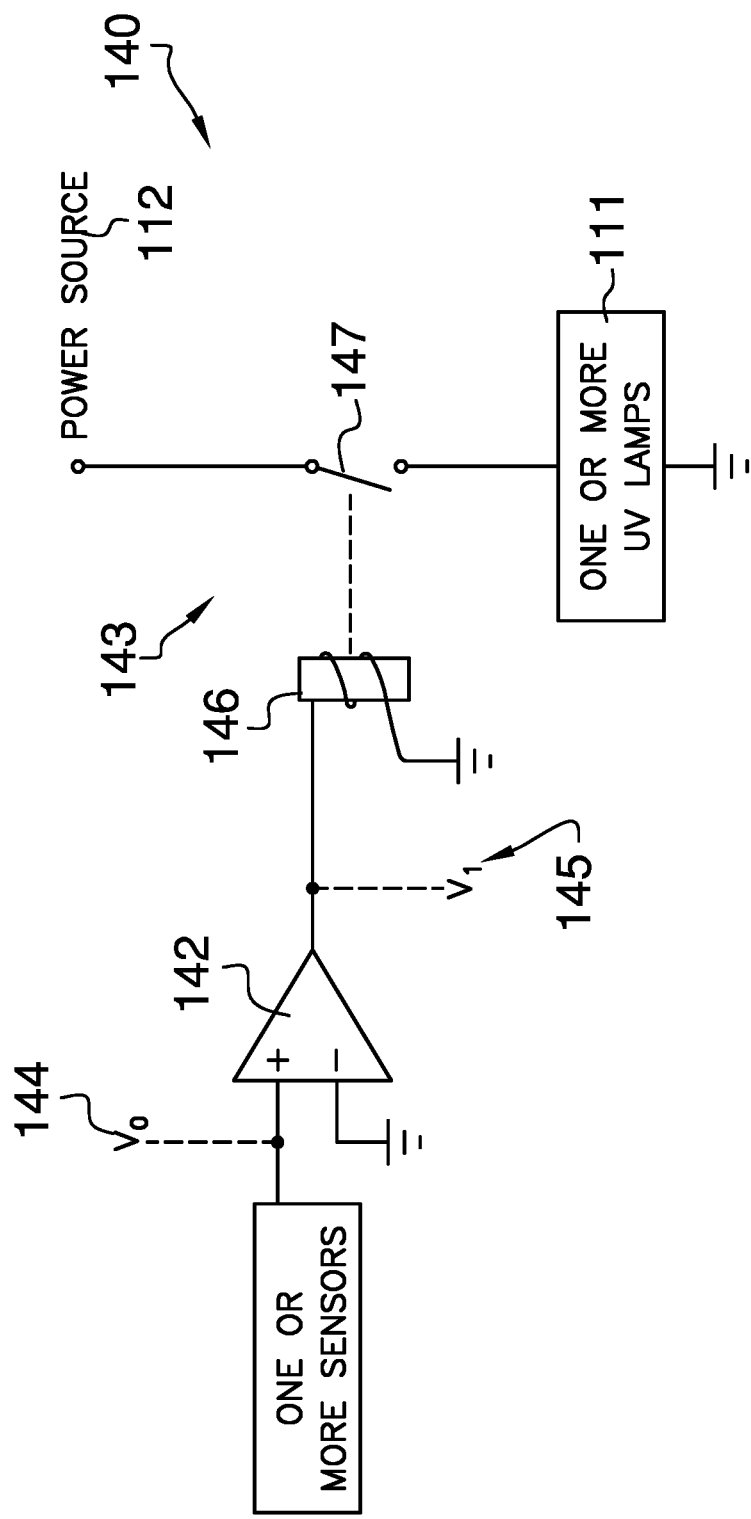
FIG. 6 is an electrical schematic of an embodiment of the disclosure.

In the first potential embodiment of the disclosure, as shown most clearly in FIG. 2, the power source 112 is a battery 141. The one or more sensors 113 is an electrical device that detects when the toilet seat 101 is in use. As shown in FIG. 6, the one or more sensors 113 are configured such that while the toilet seat 101 is in use, each of the plurality of UV sources 102 are deactivated. When the toilet seat 101 is released from use, the one or more sensors 113 are configured to reactivate each of the plurality of UV sources 102. Each of the one or more sensors 113 are selected from the group consisting of pressure sensors, proximity sensors, or radiation sensors wherein the radiation sensors are further configured to detect visible light or infrared radiation.

As shown most clearly in FIG. 6, the one or more sensors 113 are configured in an electrical system 140 that further comprises an amplifier 142 and a relay 143. The relay 143 is a commercially available relay with a switch in the normally closed position. Each of the one or more sensors 113 is configured to generate a first voltage, V0 144, when it is detected that the toilet seat 101 is in use. When the amplifier 142 detects V0 144, the amplifier 142 generates a second voltage V1 145 which is used to activate the coil 146 of the relay 143. Once the coil 146 of the relay 143 is activated, the switch 147 of the relay 143 is opened which deactivates one or more UV lamps 111 and, by implication, the plurality of UV sources 102.

In the first potential embodiment of the disclosure, as shown most clearly in FIG. 2, the plurality of UV sources 102 further comprises a first UV source 151 and a second UV source 152.

Once a traditional toilet seat is replaced with the invention 100, no special operating procedures beyond regularly scheduled maintenance is required. The toilet seat 101 may be used normally.

The components of the toilet seat 101 is formed from molded plastic. The components of the each of the plurality of UV sources 102 are commercially available.

The following definitions were used in this disclosure:

Battery: As used in this disclosure, a battery is a container consisting of one or more cells, in which chemical energy is converted into electricity and used as a source of power.

Relay: As used in this disclosure, a relay is an automatic electromagnetic or electromechanical device that reacts to changes in voltage or current by opening or closing a switch in an electric circuit.

Sensor: As used in this disclosure, a sensor is a device that receives and responds in a predetermined way to a signal or stimulus.

Ultraviolet Light: As used in this disclosure, ultraviolet light is understood to be electromagnetic radiation with a wavelength lesser than visible light. In general usage, ultraviolet light is taken to mean electromagnetic radiation with a wavelength less than 400 nm.

Ultraviolet C Light: As used in this disclosure, ultraviolet C light is understood to be ultraviolet light with wavelengths in the range of 200 nm to 300 nm. Ultraviolet C light is considered to be the most effective light for disinfection. Within the ultraviolet C range, the most effective disinfection is considered to occur with radiation wavelengths between 248 nm and 262 nm.

UV: As used in this disclosure, UV is an abbreviation for ultraviolet.

With respect to the above description, it is to be realized that the optimum dimensional relationship for the various components of the invention described above and in FIGS. 1 through 6, include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A domestic article comprising:
a toilet seat and a plurality of UV sources;
wherein the domestic article is adapted for use with a toilet;
wherein the domestic article is a seat adapted for use with the toilet;
wherein the domestic article is made of a transparent material;
wherein integrated into the structure of the toilet seat are a plurality of UV sources;
wherein the ultraviolet light sanitizes the toilet seat between uses;
wherein the toilet seat is designed as a replacement for the traditional toilet seat used with toilets;
wherein the toilet seat is molded from a transparent plastic;
wherein the transparent plastic used to mold the toilet seat is selected from the group consisting of polycarbonate or poly(methyl methacrylic);
wherein the toilet seat further comprises a plurality of UV chambers;
wherein each of the plurality of UV chambers is a cavity formed within the toilet seat that is sized and designed to receive a UV source selected from the plurality of UV sources;
wherein each UV source selected from the plurality of UV sources is provided with a UV chamber selected from the plurality of UV chambers;
wherein each UV chamber selected from the plurality of UV chambers further comprises an individual UV cavity, an access port, and an access panel.

2. The domestic article according to claim 1 wherein the individual UV cavity is a hollow space that is formed within the toilet seat.

3. The domestic article according to claim 2 wherein the access port is an aperture formed within the individual UV cavity.

4. The domestic article according to claim 3 wherein the access panel is a barrier that is designed to fit over the access port.

5. The domestic article according to claim 4 wherein the access panel is attached to the access port.

6. The domestic article according to claim 5 wherein each of the plurality of UV sources generates an ultraviolet light.

7. The domestic article according to claim 6 wherein each of the plurality of UV sources further comprises a UV lamp, a power source, and one or more sensors.

8. The domestic article according to claim 7 wherein the UV lamp generates ultraviolet C light.

9. The domestic article according to claim 8 wherein each of one or more sensors is an electrical device that detects when the toilet seat is in use.

10. The domestic article according to claim 9 wherein of the one or more sensors are selected from the group consisting of pressure sensors, proximity sensors, or radiation sensors.

11. The domestic article according to claim 9 wherein each of the one or more sensors is configured in an electrical system that further comprises an amplifier and a relay.

\* \* \* \* \*